United States Patent
Gao et al.

(10) Patent No.: US 12,070,061 B2
(45) Date of Patent: Aug. 27, 2024

(54) CARTRIDGE FOR DRY VAPORIZABLE MATERIAL

(71) Applicant: MISHMOSH, LLC, San Jose, CA (US)

(72) Inventors: Ming Gao, San Jose, CA (US); Jie Niu, Beijing (CN)

(73) Assignee: MISHMOSH, LLC, San Jose, CA (US)

( * ) Notice: Subject to any disclaimer, the term of this patent is extended or adjusted under 35 U.S.C. 154(b) by 674 days.

(21) Appl. No.: 17/275,643

(22) PCT Filed: Sep. 14, 2018

(86) PCT No.: PCT/US2018/051018
§ 371 (c)(1),
(2) Date: Mar. 11, 2021

(87) PCT Pub. No.: WO2020/055416
PCT Pub. Date: Mar. 19, 2020

(65) Prior Publication Data
US 2022/0053826 A1    Feb. 24, 2022

(51) Int. Cl.
*A24F 40/42*  (2020.01)
*A24F 40/20*  (2020.01)
*B33Y 80/00*  (2015.01)

(52) U.S. Cl.
CPC ............ *A24F 40/42* (2020.01); *A24F 40/20* (2020.01); *B33Y 80/00* (2014.12)

(58) Field of Classification Search
CPC ........... A24F 40/42; A24F 40/20; B33Y 80/00

USPC ........................................................ 131/329
See application file for complete search history.

(56) References Cited

U.S. PATENT DOCUMENTS

| | | | |
|---|---|---|---|
| 9,675,109 B2* | 6/2017 | Monsees | A24F 40/42 |
| 10,076,137 B2* | 9/2018 | Krietzman | H05B 1/0244 |
| 2005/0169814 A1 | 8/2005 | Rosenthal | |
| 2007/0283972 A1 | 12/2007 | Monsees et al. | |
| 2012/0000477 A1 | 1/2012 | Sebastian et al. | |
| 2015/0128976 A1 | 5/2015 | Verleur et al. | |
| 2016/0235122 A1 | 8/2016 | Krietzman | |
| 2016/0345630 A1 | 12/2016 | Mironov et al. | |

OTHER PUBLICATIONS

International Preliminary Report on Patentability dated Mar. 25, 2021 for International Application PCT/US2018/051018 from U.S. Receiving Office, pp. 1-7, United States.
International Search Report & Written Opinion dated Jan. 7, 2019 for International Application PCT/US18/51018 from U.S. Receiving Office, pp. 1-8, United States.

* cited by examiner

*Primary Examiner* — Gary F Paumen
(74) *Attorney, Agent, or Firm* — Sherman IP LLP; Kenneth L. Sherman; Hemavathy Perumal (57) ABSTRACT

One embodiment provides a cartridge comprising a body for maintaining dry vaporizable material. The body is shaped to fit into an oven of a vaporization device. The cartridge further comprises one or more perforations disposed on one or more sides of the body, and one or more projections extending from the body. The cartridge is directly insertable into the oven for vaporization of the dry vaporizable material.

16 Claims, 10 Drawing Sheets

CARTRIDGE FOR DRY VAPORIZABLE MATERIAL

TECHNICAL FIELD

One or more embodiments of the invention relate generally to electronic inhalation devices, and in particular, a cartridge for dry vaporizable material.

BACKGROUND

A vaporizer is an electronic inhalation device used to vaporize substances (i.e., vaporizable material) for inhalation. Examples of different vaporizable material include dry vaporizable material such as, but are not limited to, dry herb substances like cannabis, tobacco, or other dry herbs or blends. Vaporizers decrease the irritating and harmful effects of smoking, such as reducing or avoiding smoke and toxins associated with combustion. Further, with advancements in battery technology, portable vaporizers are now readily available. As such, there has been an uptick in use of vaporizers in recent times. For example, dry herb vaporizers (i.e., vaporizers configured for vaporizing dry vaporizable material only) are now popular among cannabis users and tobacco users. Colloquially, a vaporizer is also known as a vape, a vape pen, an electronic cigarette (e-cigarette), etc.

SUMMARY

One embodiment provides a cartridge comprising a body for maintaining dry vaporizable material. The body is shaped to fit into an oven of a vaporization device. The cartridge further comprises one or more perforations disposed on one or more sides of the body, and one or more projections extending from the body. The cartridge is directly insertable into the oven for vaporization of the dry vaporizable material.

These and other features, aspects and advantages of the one or more embodiments of the invention will become understood with reference to the following description, appended claims and accompanying figures.

DETAILED DESCRIPTION

The following description is made for the purpose of illustrating the general principles of one or more embodiments of the invention and is not meant to limit the inventive concepts claimed herein. Further, particular features described herein can be used in combination with other described features in each of the various possible combinations and permutations. Unless otherwise specifically defined herein, all terms are to be given their broadest possible interpretation including meanings implied from the specification as well as meanings understood by those skilled in the art and/or as defined in dictionaries, treatises, etc.

One or more embodiments of the invention relate generally to electronic inhalation devices, and in particular, a cartridge for dry vaporizable material. One embodiment provides a cartridge comprising a body for maintaining dry vaporizable material. The body is shaped to fit into an oven of a vaporization device. The cartridge further comprises one or more perforations disposed on one or more sides of the body, and one or more projections extending from the body. The cartridge is directly insertable into the oven for vaporization of the dry vaporizable material.

A multitude of issues may arise when using a dry herb vaporizer. For example, as dry herb substances are commonly available/popular in loose-leaf form or powder form, a user of a dry herb vaporizer may find that the experience of loading (i.e., adding) dry herb substances directly into an oven of the vaporizer prior to inhalation particularly inconvenient, especially in difficult situations or contexts such as when the user is traveling. Discharging or dispensing dry herb substances from the vaporizer after use is similarly inconvenient as the user must manually extract or pull out the dry herb substances out of the oven and then dispose of it. While there are accessories or tools that a user may utilize to facilitate such tasks, it becomes cumbersome for the user to have to carry or transport additional items such as the accessories or tools. Furthermore, as a size of the oven is fixed, the user may have to tightly press or pack the dry herb substances into the oven to obtain more vapor from the vaporizer.

Furthermore, dry herb substances loaded into the oven may not heat evenly during vaporization, even when a heating temperature of the oven is set to a maximum. As a result, a portion of the dry herb substances may not be completely consumed after use, which is a product waste and money waste.

As another example, the oven itself is susceptible to discoloration as dry herb substances may stain the oven when directly loaded into the oven. Additionally, integrity/ quality of dry herb substances may be compromised during shipping and storing, especially when exposed to moist or dry environmental/weather conditions. There arises a need for better packaging of dry herb substances to prevent deterioration in integrity/quality of the substances.

While there are conventional solutions for packaging liquid substances (e.g., e-liquids, essential oils, etc.) for ease of use in vaporizers configured for vaporizing liquid substances, such as liquid-filled capsules (e.g., capsules filled with Cannabidiol oil), there are no existing solutions for packaging dry substances for ease of use in dry herb vaporizers. Furthermore, it is not possible to utilize such liquid-filled capsules in dry herb vaporizers.

Embodiments of the invention provide solutions for packaging dry vaporizable material to improve user experience with dry herb vaporizers. Embodiments of the invention provide a low-cost, compact packaging solution for dry vaporizable materials. One embodiment provides a removable cartridge including dry vaporizable material for use within an oven of a dry herb vaporizer. A user can directly load the cartridge into the oven without use of accessories or tools. In one embodiment, the cartridge includes a plurality of perforations (i.e., holes) that facilitate air flow during vaporization of the dry vaporizable material. In one embodiment, the cartridge includes one or more projections (e.g., handles, tabs, flanges, flaps, etc.) that the user can hold onto to easily remove or pull out (i.e., unload) the cartridge from the oven after use. In one embodiment, the cartridge is available for one time use only (i.e., can only be used once); the user must load a new cartridge into the oven for each subsequent use of the dry herb vaporizer. For example, the cartridge may be made of low-cost material such as, but not limited to, disposable aluminum foil, different types of cigar wrapper, cellophane wrappers, recyclable glass, graphene, etc. In another embodiment, the cartridge is re-usable (e.g., the user can re-fill the cartridge with dry vaporizable material). In one embodiment the cartridge can be used with different types of dry herb vaporizers without modifications to the vaporizers, such as commonly available/popular vape pens.

Figure 1:
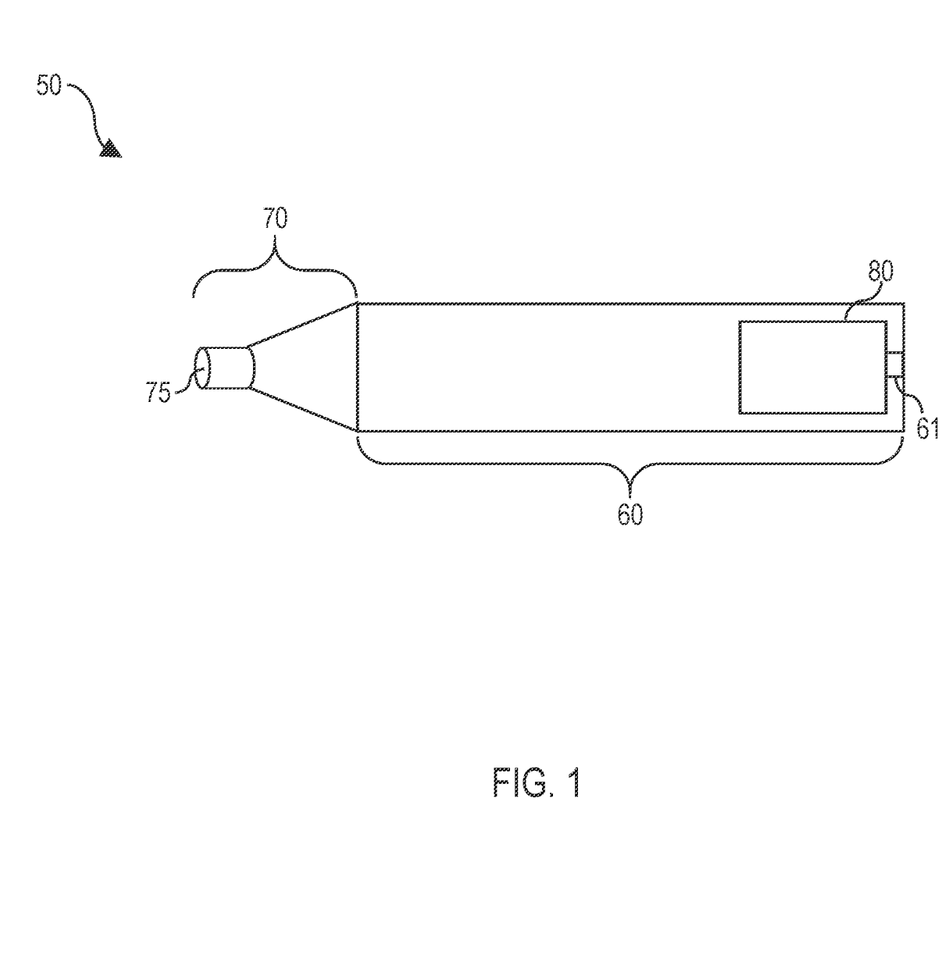
FIG. 1 illustrates an example dry herb vaporization device.
Figure 2:
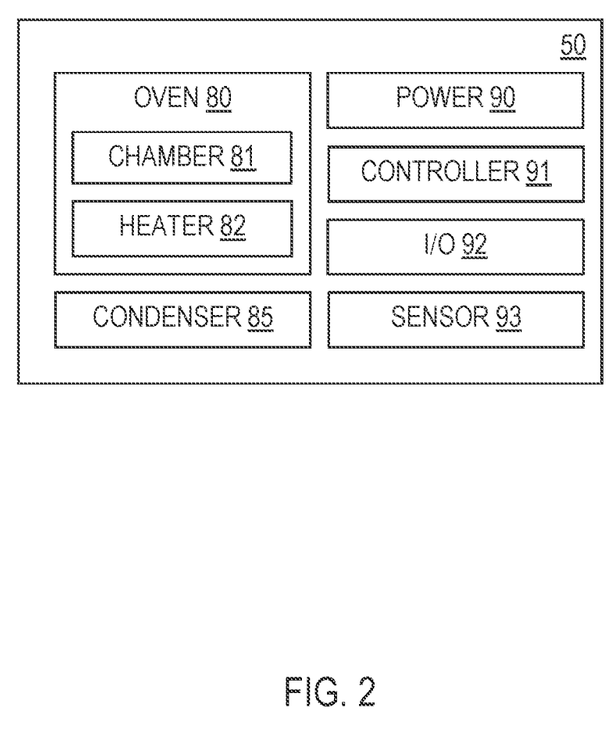
FIG. 2 is a block diagram of different components included in the vaporization device in FIG. 1.

FIG. 1 illustrates an example dry herb vaporization device 50. FIG. 2 is a block diagram of different components included in the vaporization device 50 in FIG. 1. The device 50 comprises a body 60 configured to maintain (i.e., house), integrate and/or couple with one or more components of the device 50.

For example, the body 60 is configured to detachably couple to or integrate with a mouthpiece 70. The mouthpiece 70 may be coupled to or integrated with the body 60 at a top end of the body 60. The mouthpiece 70 may be flexible and ergonomically designed for a comfortable fit. A user may inhale vapor resulting from vaporization via an outlet 75 of the mouthpiece 70.

The body 60 includes one or more air flow inlets 61. Air is drawn/pulled into the device 50 via the one or more air flow inlets 61. For example, the one or more air flow inlets 61 may be disposed at a bottom end of the body 60 opposite the mouthpiece 70. As another example, the one or more air flow inlets 61 may be disposed at one or more other regions of the body 60. Inhalation by a user through the outlet 75 of the mouthpiece 70 creates a suction that draws/pulls air through the one or more airflow inlets 61.

The body 60 is configured to maintain or integrate with an oven 80. The oven 80 comprises an oven chamber (i.e., receptacle) 81 for receiving and maintaining dry vaporizable material, and a heater 82 for heating the dry vaporizable material. The heater 82 may be in direct contact with the oven chamber 81 (e.g., surrounding the oven chamber 81). The heater 82 may transfer heat to dry vaporizable material maintained in the oven chamber 81 via conductive, convective, and/or radiative heat transfer. The oven 80 may be disposed proximate to the bottom end of the body 60 to provide a user with easy access when loading dry vaporizable material into, or removing dry vaporizable material from after use, the oven chamber 81.

During vaporization, the heater 82 heats the dry vaporizable material maintained in the oven chamber 81 and air drawn/pulled through the one or more airflow inlets 61 to generate vapors. The body 60 is configured to maintain or integrate with a condenser 85. Vapors generated during vaporization are drawn/pulled out of the oven 80 and into the condenser 85 where the vapors expand, cool and condense to form an inhalable aerosol that is drawn/pulled out of the mouthpiece 70 through the outlet 75 (e.g., by inhalation by a user). The device 50 includes one or more air flow channels or paths (not shown) for propagating vapors and a resulting aerosol between the one or more air flow inlets 61, the oven 80, the condenser 85, the mouthpiece 70, and the outlet 75.

The device 50 may include one or more of the following: a power source 90 (e.g., a replaceable or rechargeable battery), one or more sensor units 93 (e.g., a temperature sensor, pressure sensor, etc.), one or more input/output (I/O) units 92 (e.g., one or more indicator lights, one or more switches such as an on/off switch, a temperature regulator switch, etc.), and a controller 91 for controlling operation of the device 50 based sensor data captured by the one or more sensor units 93 and/or state of the one or more I/O units 92 (e.g., activating the heater 82 based on sensor data from the pressure sensor indicating that a suction has been created via the outlet 75 of the mouthpiece 70, controlling temperature of the heater 82 based on a state of the temperature regulator switch, etc.).

Figure 3:
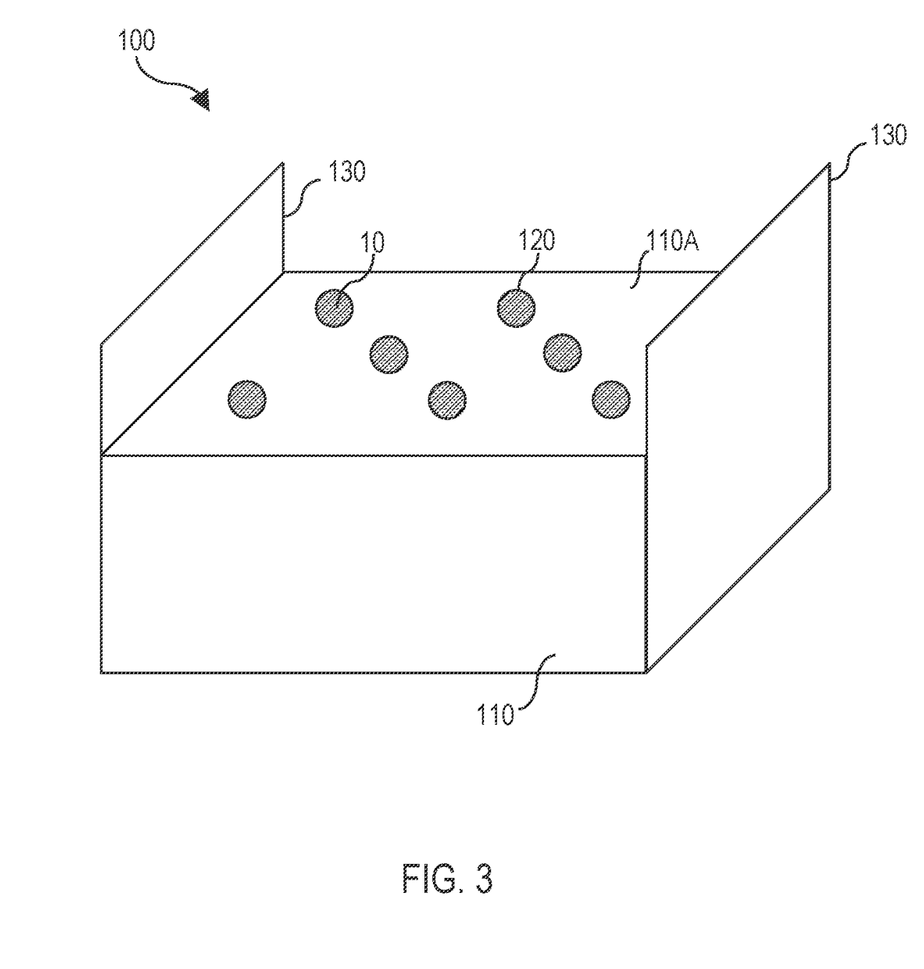
FIG. 3 illustrates a top perspective view of an example removable cartridge for use in an oven of a dry herb vaporizer (e.g., the dry herb vaporization device in FIGS. 1-2), in one or more embodiments of the invention.
Figure 4:
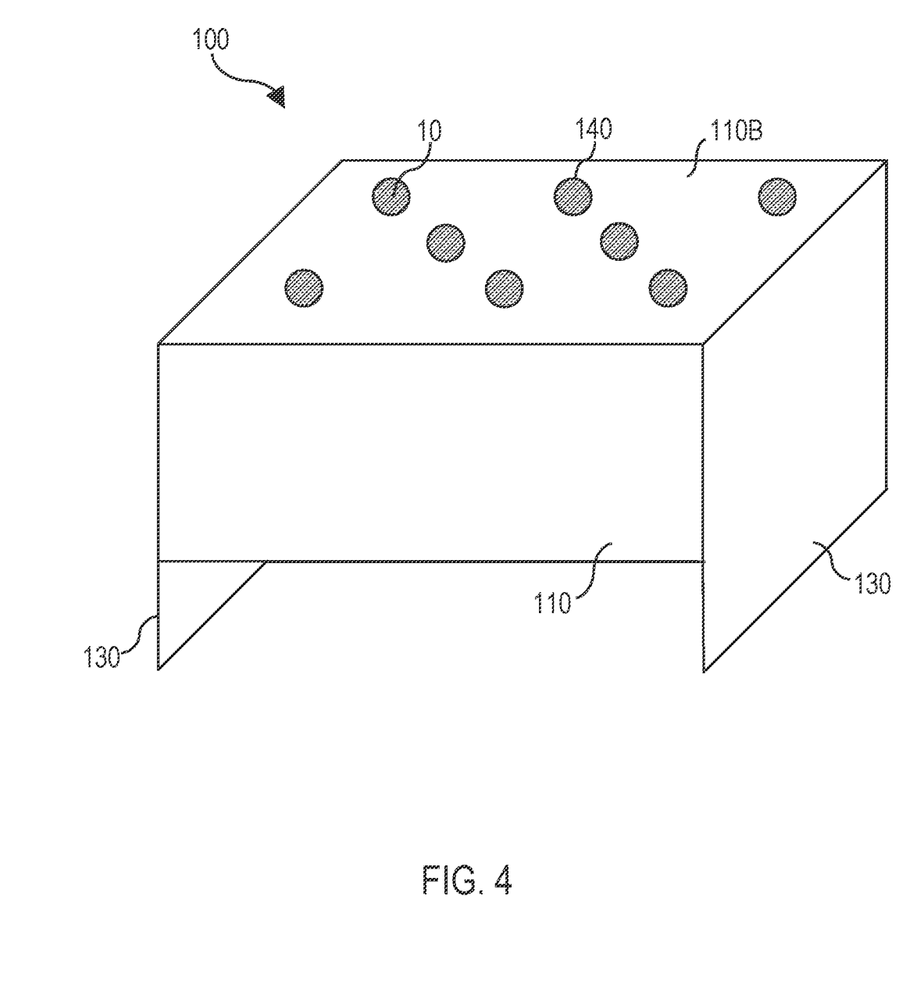
FIG. 4 illustrates a bottom perspective view of the removable cartridge in FIG. 3, in one or more embodiments of the invention.

FIG. 3 illustrates a top perspective view of an example removable cartridge 100 for use in an oven of a dry herb vaporizer (e.g., the dry herb vaporization device 50 in FIGS. 1-2), in one or more embodiments of the invention. FIG. 4 illustrates a bottom perspective view of the removable cartridge 100 in FIG. 3, in one or more embodiments of the invention. The cartridge 100 comprises a body 110 for housing or maintaining dry vaporizable material 10. In one embodiment, the body 110 is compact and designed/shaped to fit tightly into an oven 80 of different types of dry herb vaporizers. For example, the cartridge 100 is suitable for use in commonly available/popular dry herb vaporizers without requiring any modifications to the vaporizers itself.

The body 110 may have different shapes such as, but not limited to, a rectangular shape, a cylindrical shape, a spherical shape, an oblong shape, etc.

In one embodiment, the body 110 is made out of one or more affordable/low-cost and/or recyclable materials such as, but not limited to, disposable aluminum foil, different types of cigar wrapper, cellophane wrappers, recyclable glass, graphene, etc.

In one embodiment, the body 110 is suitable for maintaining different types of dry vaporizable material 10 such as, but not limited to, cannabis, tobacco, or other dry herbs or blends (e.g., dry herbs mixed with mint, tea leaves, etc.) in loose-leaf form, powder form, etc. This allows different flavors of cartridges 100 to be manufactured. The body 110 is sealed to prevent the dry vaporizable material 10 contained inside from leaking/pouring out, thereby reducing or minimizing product waste and money waste.

In one embodiment, dry vaporizable material 10 is pressed/stuffed tightly inside the body 110 to generate more vapor, thereby prolonging a user's vaping experience. In another embodiment, dry vaporizable material 10 is pressed/stuffed loosely inside the body 110 to generate less vapor, thereby shortening a user's vaping experience. The degree of tightness at which dry vaporizable material 10 is pressed/stuffed inside the body 110 may be customized during the manufacturing process of cartridges 100 based on customer preferences.

In one embodiment, the cartridge 100 may be embodied as a pod or a capsule. The cartridge 100 represents an individual package of dry vaporizable material for direct use in a dry herb vaporizer.

Different brands or models of dry herb vaporizers include ovens of different physical dimensions (e.g., depth) and/or shapes. In one embodiment, cartridges 100 of different physical dimensions, shapes and/or materials intended for different brands or models of dry herb vaporizers are manufactured/produced. A desired size and/or shape of a cartridge 100 is based on a size and shape of an oven the cartridge 100 is intended for.

An amount or quantity of dry vaporizable material 10 included in a cartridge 100 is based on at least one of the following factors: physical dimensions of the cartridge 100, a shape of the cartridge 100, material(s) that the cartridge 100 is made out of.

In one embodiment, for an oven shaped to accommodate about 0.3 grams of dry vaporizable material 10, a cartridge 100 intended for the oven is packed with up to 0.3 grams of dry herbs. If the cartridge 100 is made out of aluminum foil, a gross weight of the cartridge 100 is within a range of substantially about 0.3 grams to 1.5 grams. If the oven is fully packed with the cartridge 100 containing 0.3 grams of dry herbs, a user is able to extract 15 to 25 draws from the cartridge 100.

A user can load/plug the cartridge 100 directly into an oven 80 of a dry herb vaporizer without use of accessories or tools. Further, as the cartridge 100 is designed/shaped to fit tightly into an oven 80, an oven chamber 81 of the oven 80 is sealed tight (e.g., an air tight seal) with the cartridge 100 when the cartridge 100 is loaded/plugged into the oven chamber 81. This allows a heater 82 of the oven 80 to evenly heat dry vaporizable material 10 contained inside the cartridge 100 during vaporization, thereby ensuring that the dry vaporizable material 10 is entirely consumed after use and in turn reducing or minimizing product waste and money waste. Further, it is much more convenient for the user to travel with pre-packaged individual cartridges 100 instead of containers of loose-leaves or powder.

In one embodiment, as a result of infrared heat wave convection with the material(s) the cartridge 100 is made out of (e.g., aluminum foil), the dry vaporizable material 10 inside the cartridge 100 is heated more evenly by the heater 82 (instead of the heater 82 heating the dry vaporizable material directly in conventional solutions).

In one embodiment, the cartridge 100 is available for one time use only (i.e., can only be used once); the user must load a new cartridge 100 into the oven 80 for each subsequent use of the dry herb vaporizer. In another embodiment, the cartridge 100 is re-usable (e.g., the user can re-fill the cartridge 100 with dry vaporizable material).

The cartridge 100 reduces/minimizes staining to the oven 80 as dry vaporizable material 10 contained inside the cartridge 100 is not in direct contact with any portion of the oven 80. Additionally, containing dry vaporizable material 10 inside the cartridge 100 prevents/minimizes deterioration in integrity/quality of the material 10 during shipping and storing.

In one embodiment, one or more sides of the body 110 includes one or more perforations (i.e., holes) that facilitate air flow during vaporization of dry vaporizable material 10 contained inside the body 110. In one embodiment, only a top side 110A of the body 110 includes perforations. In another one embodiment, only a bottom side 110B of the body 110 includes perforations. In yet another embodiment, both the top side 110A and the bottom side 110B of the body 110 includes perforations.

For example, as shown in FIGS. 3-4, in one embodiment, the top side 110A includes a first plurality of perforations 120, and the bottom side 110B includes a second plurality of perforations 140. Each plurality of perforations 120, 140 are spaced apart. In one embodiment, the plurality of perforations 120 on the top side 110A may be arranged similarly or differently to the plurality of perforations 140 on the bottom side 110B.

In one embodiment, each plurality of perforations 120, 140 are distributed across the top side 110A, the bottom side 110B in such a manner to create an air flow during vaporization that improves a user's vaping experience. For example, each of the plurality of perforations 120,140 are disposed/positioned to create a restricted air flow within the vaporizer, resulting in an aerosol that feels good to the user (e.g., provides the user with a smoother feel when inhaling the aerosol).

In one embodiment, one or more other sides of the body 110 includes perforations, such as sidewalls extending from the top side 110A/bottom side 110B at opposite edges of a transverse width/longitudinal length of the top side 110A/bottom side 110B.

In one embodiment, the cartridge 100 includes one or more projections (e.g., handles, tabs, flanges, flaps, etc.) extending from the body 110. The one or more projections are located/disposed such that a user can directly hold/grip/pick up the one or more projections to easily extract/remove/pull out the cartridge 100 from the oven 80 after consumption. As shown in FIGS. 3-4, in one embodiment, the one or more projections include a pair of projections 130 extending from opposing sides of the body 110. The user may also use accessories or tools to retrieve the cartridge 100 from the oven 80.

In one embodiment, the one or more projections are designed/shaped to quickly disperse/transfer heat away, thereby preventing burns to a user's fingers or hand when the user retrieves the cartridge 100 from the oven 80 after consumption. The body 110 and the one or more projections may comprise of the same material or different materials.

For example, in one embodiment, the one or more projections comprises one or more handles made out of thin aluminum. The handles may have a lower temperature than the body 110 itself, thereby enabling the user to safely retrieve the cartridge 100 from the oven 80 via the handles without burning himself/herself. Further, the amount of time required for the user to wait before removing the cartridge 100 is reduced, thereby improving the user's vaping experience (e.g., the user can re-load with another cartridge 100 quickly instead of having to wait for a few minutes). In another embodiment, the one or more projections 100 may have a different structure and/or comprise of a different material. Further, as the consumed dry vaporizable material 10 is entirely contained inside the cartridge 100, the user can simply dispose the cartridge 100 if the cartridge 100 is available for one time use only.

A user can carry the cartridge 100, load the cartridge 100 into the oven 80, and remove the cartridge 100 from the oven 80 after consumption easily without having to worry about leakage or spilling loose-leaves or powder.

In one embodiment, a body 110 of a cartridge 100 is manufactured/produced to have a substantially rectangular shape with the following physical dimensions: substantially about 20 millimeters (mm) in length, substantially about 8 mm in height, and substantially about 8 mm in width. In one embodiment, each perforation 120, 140 on the body 110 has a diameter of a substantially less than 1 mm. In one embodiment, a thickness of each wall of the body 110 (e.g., the top side 110A, the bottom side 110B, the sidewalls) is substantially about 0.1 mm.

Figure 5:
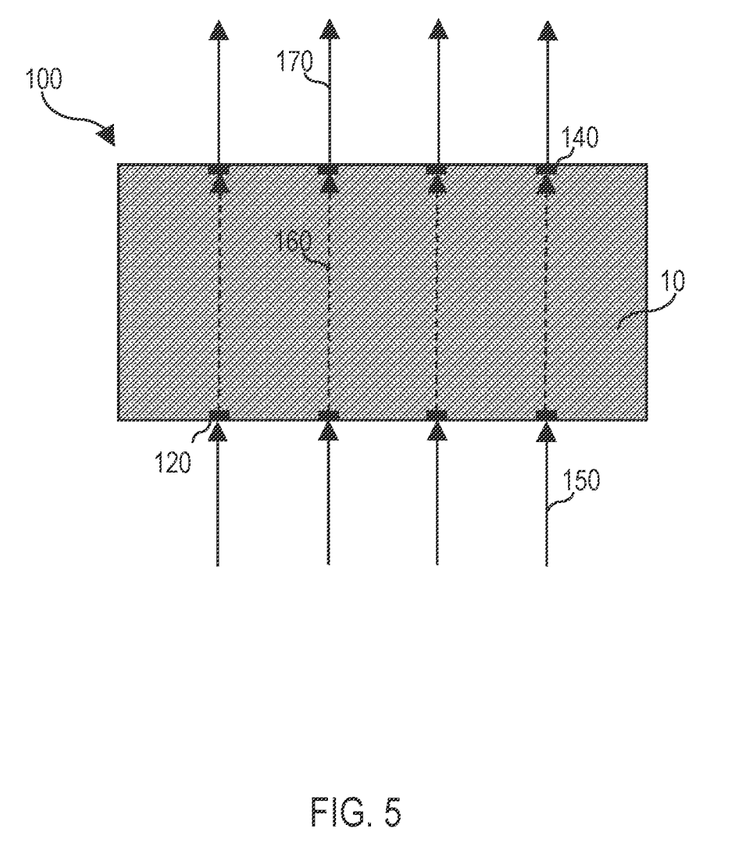
FIG. 5 illustrates a cross-section view of example airflow inside a removable cartridge used in an oven of a dry herb vaporizer (e.g., the dry herb vaporization device in FIGS. 1-2) during vaporization, in one or more embodiments of the invention.

FIG. 5 illustrates a cross-section view of example airflow inside a removable cartridge 100 used in an oven of a dry herb vaporizer (e.g., the dry herb vaporization device 50 in FIGS. 1-2) during vaporization, in one or more embodiments of the invention. In one embodiment, the plurality of perforations 120 on the top side 110A of the cartridge 100 are aligned with the plurality of perforations 140 on the bottom side 110B of the cartridge 100. The alignment of the perforations 120, 140 restricts flow of air 150 drawn/pulled via one or more air flow inlets (e.g., air flow inlet 61 in FIG. 1) of the vaporizer to one or more air flow paths 160 inside the cartridge 100. Vapors 170 generated during the vaporization are propagated via more air flow channels or paths of the vaporizer to form an inhalable aerosol that feels good to the user (e.g., a smooth and even feel) when the user draws the aerosol out of a mouthpiece (e.g., mouthpiece 70 in FIG. 1) of the vaporizer by inhalation. The restricted air flow improves the user's vaping experience.

Figure 6A:
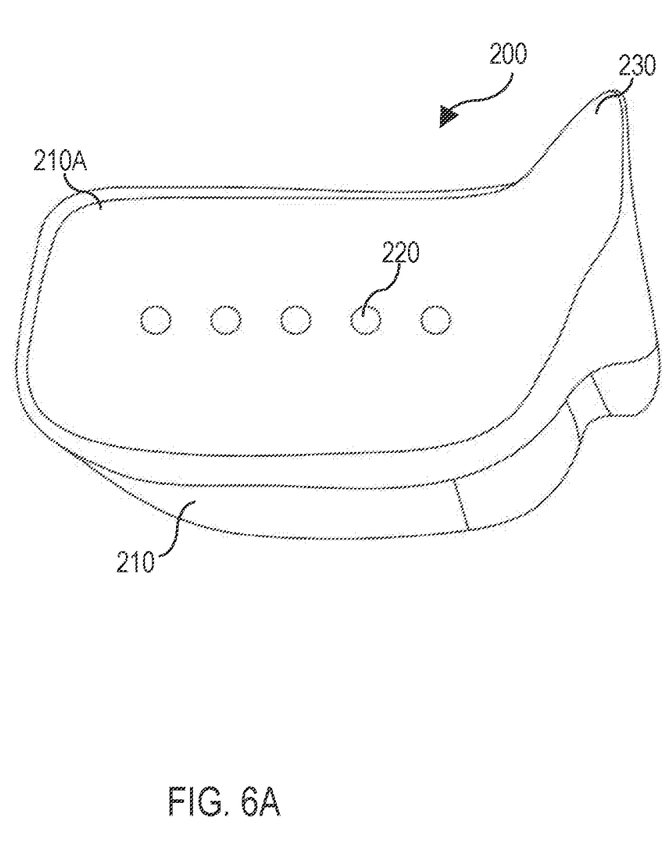
FIG. 6A illustrates a top perspective view of another example removable cartridge for use in an oven of a dry herb vaporizer (e.g., the dry herb vaporization device in FIGS. 1-2), in one or more embodiments of the invention.
Figure 6B:
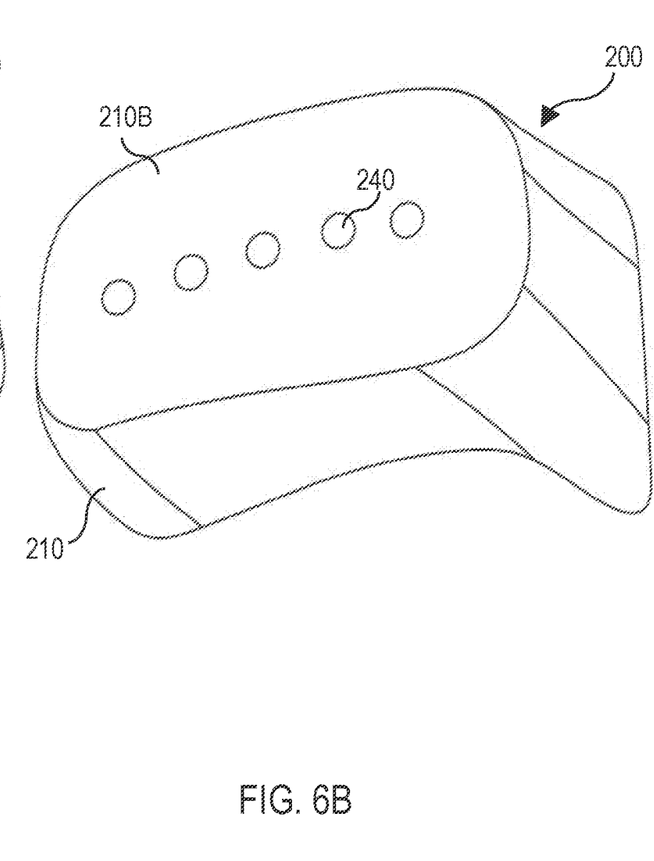
FIG. 6B illustrates a bottom perspective view of the removable cartridge in FIG. 5, in one or more embodiments of the invention.
Figure 7:
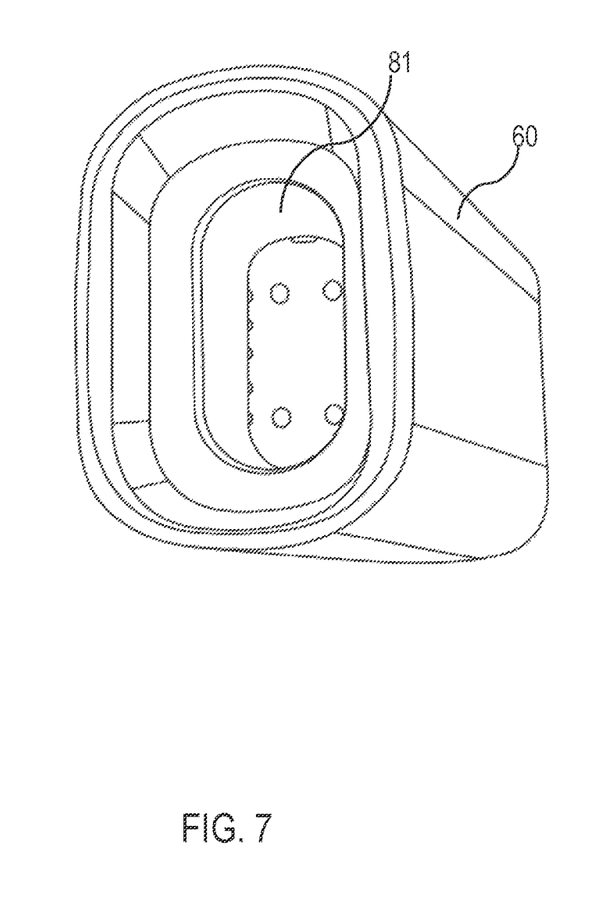
FIG. 7 illustrates an example oven of a dry herb vaporizer that the removable cartridge in FIGS. 6A-6B is shaped to fit in, in one or more embodiments of the invention.
Figure 8:
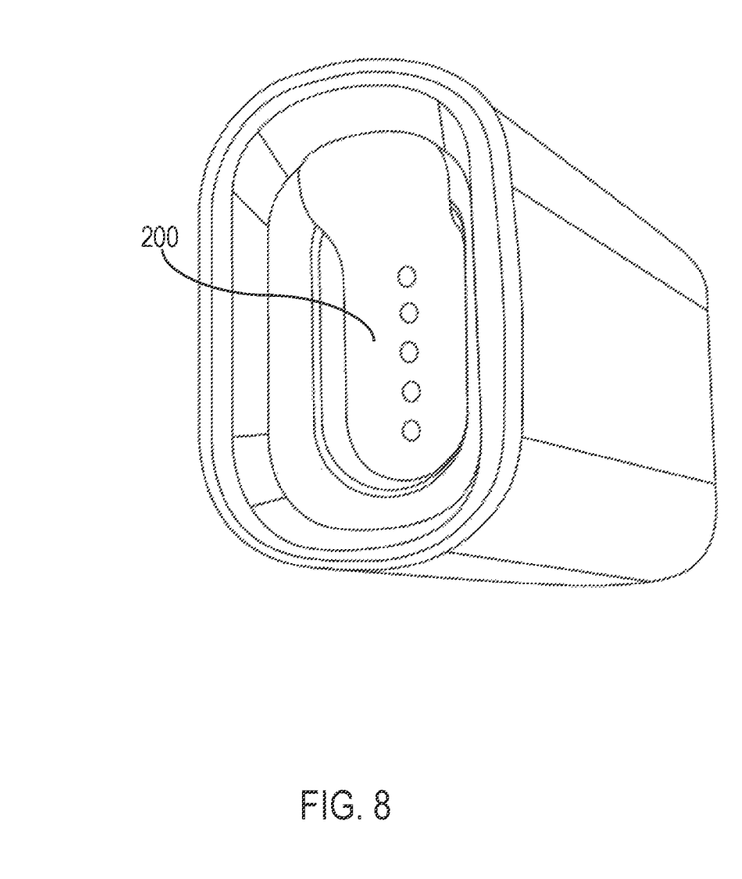
FIG. 8 illustrates the removable cartridge in FIGS. 6A-6B loaded into the oven in FIG. 7, in one or more embodiments of the invention.

FIG. 6A illustrates a top perspective view of another example removable cartridge 200 for use in an oven of a dry herb vaporizer (e.g., the dry herb vaporization device 50 in FIGS. 1-2), in one or more embodiments of the invention. FIG. 6B illustrates a bottom perspective view of the removable cartridge 200 in FIG. 6A, in one or more embodiments of the invention. FIG. 7 illustrates an example oven 80 of a dry herb vaporizer that the removable cartridge 200 is shaped to fit in, in one or more embodiments of the invention. FIG. 8 illustrates the removable cartridge 200 loaded into the oven 80 in FIG. 7, in one or more embodiments of the invention. The cartridge 200 comprises a body 210 for housing or maintaining dry vaporizable material 10. The body 210 is compact and designed/shaped to fit tightly into an oven 80 of different types of dry herb vaporizers. A top side 210A and a bottom side 210B of the body 210 includes a first plurality of perforations 220 and a second plurality of perforations 240, respectively. The cartridge further includes a projection 230 extending from a side of the body 210. The projection 230 is used to facilitate removal of the cartridge 200 from the oven 80 after consumption.

Figure 9:
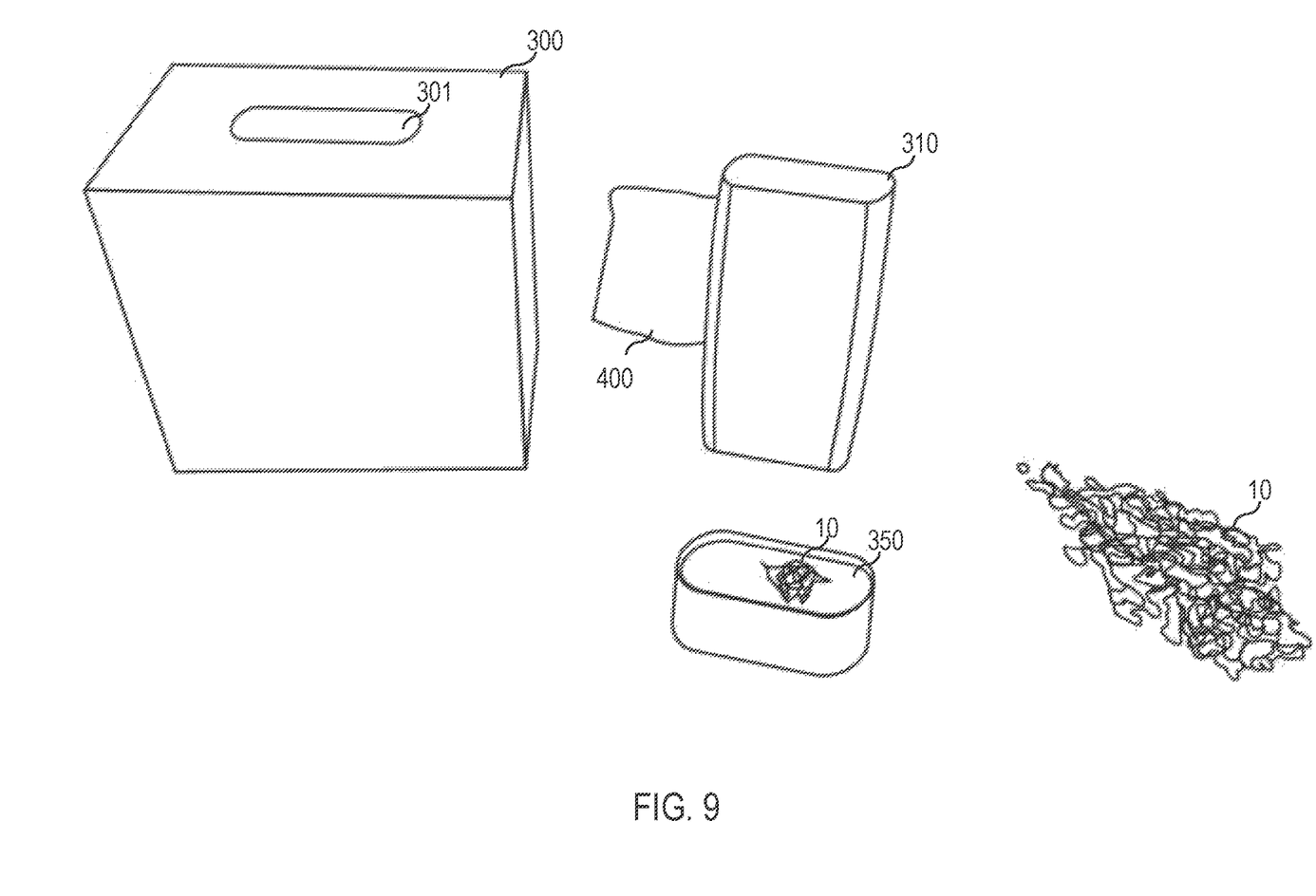
FIG. 9 illustrates a first example molding process for manufacturing cartridges, in one or more embodiments of the invention.

FIG. 9 illustrates a first example molding process for manufacturing cartridges (e.g., cartridge 100 in FIGS. 3-4, cartridge 200 in FIGS. 6A-6B), in one or more embodiments of the invention. In one embodiment, a mold 300 comprising a hollowed-out portion 301 is utilized, wherein the hollowed-out portion 301 is designed/shaped based on physical dimensions of an oven 80 the cartridge is intended for. During the molding process, the hollowed-out portion 301 is filled with a liquid or pliable material, such as metal. The material hardens or sets inside the mold 300, resulting in a part 310. The part 310 is used to assemble a cartridge that is designed/shaped to tightly fit into the oven 80.

For example, in one embodiment, for one-off production or batch production, a piece of aluminum foil 400 is wrapped around a portion of the part 310 to form a cartridge 350.

As another example, in one embodiment, for mass production, the part 310 is utilized as a component on an assembly machine configured for assembling cartridges 350.

In one embodiment, a height of the part 310 is substantially the same as a desired height of the cartridge, wherein the desired height is based on a depth of the oven 80 the cartridge is intended for.

Figure 10:
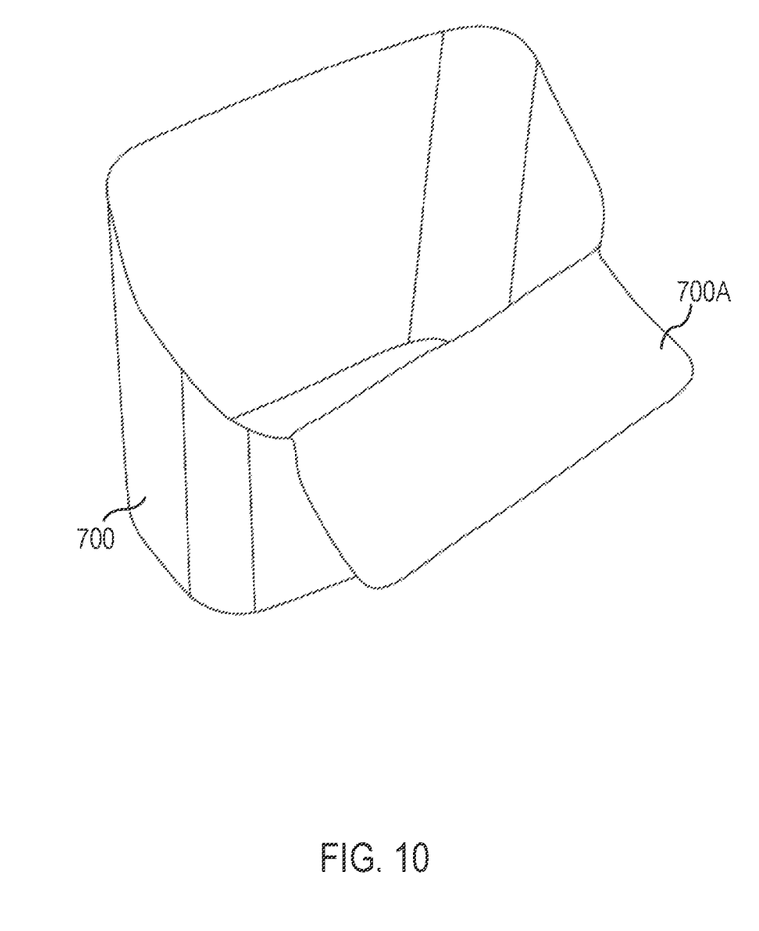
FIG. 10 illustrates an example pre-fabricated container for use in assembling cartridges, in one or more embodiments of the invention.

FIG. 10 illustrates an example pre-fabricated container 700 for use in assembling cartridges (e.g., cartridge 100 in FIGS. 3-4, cartridge 200 in FIGS. 6A-6B), in one or more embodiments of the invention. In one embodiment, for one-off production, batch production, or mass production, a pre-fabricated container 700 (e.g., a pre-folded container made out of aluminum foil) with a flap/lid 700A is formed for use in assembling a cartridge, thereby removing a need to wrap material (such as aluminum foil) around a part (e.g., part 310 in FIG. 9). The container 700 has a size and a shape substantially similar to a desired size and shape of the cartridge.

Figure 11:
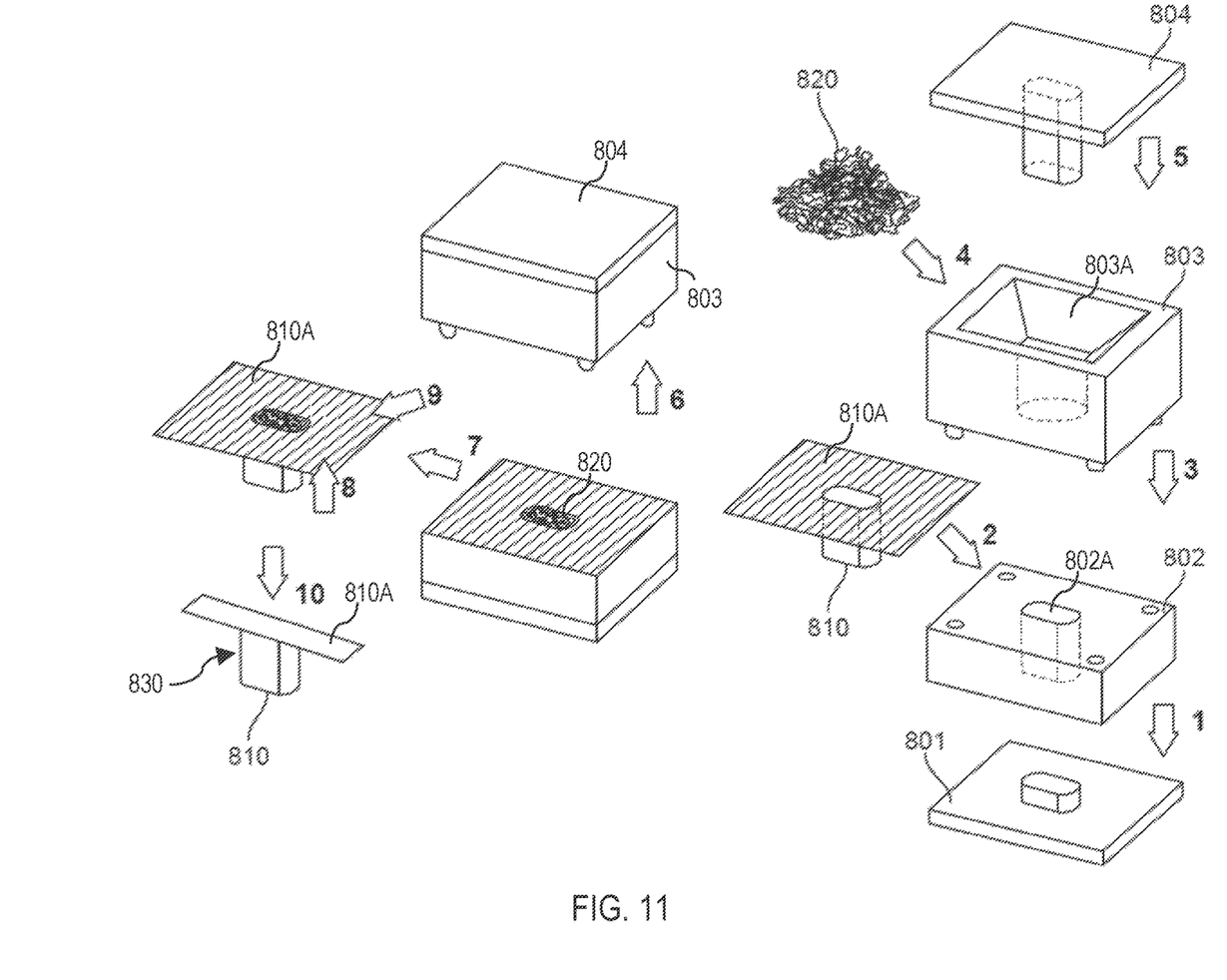
FIG. 11 illustrates a second example molding process for manufacturing cartridges, in one or more embodiments of the invention.

FIG. 11 illustrates a second example molding process for manufacturing cartridges (e.g., cartridge 100 in FIGS. 3-4, cartridge 200 in FIGS. 6A-6B), in one or more embodiments of the invention. In one embodiment, a molding process involves the following components: a bottom member 801, a mold body 802 including a hollowed-out portion 802A, a funnel 803 including a receiving portion 803A, and a press 804. The molding process is then performed as follows: First, the mold body 802 is placed on top of the bottom member 801 (this step is illustrated using reference label 1 in FIG. 11). Second, a pre-folder container 810 with a lid 810A (e.g., pre-folded container 700 in FIG. 10) is inserted into the mold body 802 via the hollowed-out portion 802A, such that a bottom of the container 810 is held and supported by the bottom member 801, and the lid 810A is spread out on top of the mold body 802 (this step is illustrated using reference label 2 in FIG. 11). Third, the funnel 803 is placed on top of the mold body 802 (this step is illustrated using reference label 3 in FIG. 11). Fourth the container 810 is filled with dry vaporizable material 820 via the funnel 803 by inserting the dry vaporizable material 820 into the receiving portion 803A (this step is illustrated using reference label 4 in FIG. 11). Fifth, the press 804 is used to press/push the dry vaporizable material 820 in the receiving portion 803A down through the funnel 803 and into the container 810 (this step is illustrated using reference label 5 in FIG. 11). Sixth, when the container 810 is filled, the funnel 803 and the press 804 are removed from the mold body 802 (this step is illustrated using reference label 6 in FIG. 11). Seventh, the filled container 810 is removed from the mold body 802 (this step is illustrated using reference label 7 in FIG. 11). Eighth, the lid 810A of the container 810 is folded to assemble/form a cartridge 830 (this step is illustrated using reference labels 8, 9 and 10 in FIG. 11).

As shown in FIG. 11, the cartridge 830 includes the container 810 as its body (e.g., body 110 in FIGS. 3-4), and the folded lip 810A as its projection (e.g., projection 130 in FIGS. 3-4).

In one embodiment, one or more perforations (e.g., perforations 120, 140 in FIGS. 3-4) are punctured into the cartridge 830 after the cartridge 830 is assembled. In another embodiment, the container 810 used to assemble the cartridge 830 during the molding process already includes one or more perforations.

As stated above, different brands or models of dry herb vaporizers may include ovens of different physical dimensions and/or shapes. In one embodiment, cartridges of different physical dimensions and/or shapes intended for ovens of different brands or models of dry herb vaporizers are manufactured/produced using different molds.

In one embodiment, manufacture/production of cartridges (e.g., cartridge 100 in FIGS. 3-4, cartridge 200 in FIGS. 6A-6B) is performed at room temperature with controlled humidity.

In one embodiment, a cartridge is manufactured via other processes such as, but not limited to, 3D scanning, 3D printing, metal works, etc.

In one embodiment, multiple cartridges are packaged into one pack for convenient shipping and storing. A user can buy a pack of cartridges and use each cartridge until the entire pack is exhausted.

In one embodiment, one or more cartridges are packaged in an airtight and sealed outer packaging (e.g., a blister pack). The outer packaging maintains moisture of dry vaporizable material inside the cartridges, protecting the material against external factors, such as humidity and contamination for extended periods of time.

References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the embodiments has been presented for purposes of illustration and description, but is not intended to be exhaustive or limited to the embodiments in the form disclosed. Many modifications and variations will be apparent to those of ordinary skill in the art without departing from the scope and spirit of the invention.

Though the embodiments have been described with reference to certain versions thereof; however, other versions are possible. Therefore, the spirit and scope of the appended claims should not be limited to the description of the preferred versions contained herein.

What is claimed is:

1. A cartridge comprising:
    a body for maintaining dry vaporizable material, wherein the body is shaped to fit into an oven of a vaporization device;
    one or more perforations disposed on one or more sides of the body; and
    a pair of projections extending from opposing sides of the body;
    wherein the cartridge is directly insertable into the oven for vaporization of the dry vaporizable material;
    wherein vapor resulting from the vaporization is drawn out of a mouthpiece of the vaporization device; and
    wherein each projection has a lower temperature than the body to enable safe removal of the cartridge, via the projection, from the oven after the vaporization.

2. The cartridge of claim 1, wherein the cartridge is a pod.

3. The cartridge of claim 1, wherein the cartridge is a capsule.

4. The cartridge of claim 1, wherein the body is rectangular in shape.

5. The cartridge of claim 1, wherein the body is cylindrical in shape.

6. The cartridge of claim 1, wherein the body is spherical in shape.

7. The cartridge of claim 1, wherein the body is oblong in shape.

8. The cartridge of claim 1, wherein the one or more perforations are distributed across the one or more sides of the body to restrict airflow within the vaporization device during the vaporization of the dry vaporizable material.

9. The cartridge of claim 1, wherein the body is made out of aluminum foil.

10. The cartridge of claim 9, wherein aluminum foil allows for the dry vaporizable material to be evenly heated during the vaporization of the dry vaporizable material.

11. The cartridge of claim 1, wherein each projection disperses heat quicker than the body after the vaporization to prevent burns to a user holding the projection.

12. The cartridge of claim 1, wherein a user removes the cartridge from the oven by holding at least one projection of the pair of projections and pulling the cartridge out of the oven via the at least one projection.

13. The cartridge of claim 1, wherein the cartridge is manufactured via at least one of the following: molding, 3D scanning, 3D printing, metal works.

14. The cartridge of claim 1, wherein the cartridge is recyclable.

15. The cartridge of claim 1, wherein the cartridge is refillable.

16. The cartridge of claim 1, wherein the cartridge is disposable after one-time use.

* * * * *